United States Patent [19]

Hermecz et al.

[11] Patent Number: 4,871,849
[45] Date of Patent: Oct. 3, 1989

[54] 1-METHYLAMINO-QUINOLINE-CARBOXYLIC ACID DERIVATIVES

[75] Inventors: István Hermecz; Géza Kereszturi; Lelle Vasvávi; Ágnes Horváth, all of Budapest; Mária Balogh, Dunakeszi; Gábor Kovács, Budapest; Tamás Szüts, Budapest; Péter Ritli, Budapest; Judit Sipos, Budapest; Anikó pA Jor, Budapest, all of Hungary

[73] Assignee: Chinoin Gyogyszer es Vegyeszeti Termekek Gyara Rt., Budapest, Hungary

[21] Appl. No.: 105,299

[22] PCT Filed: Dec. 9, 1986

[86] PCT No.: PCT/HU86/00067
§ 371 Date: Jun. 24, 1987
§ 102(e) Date: Jun. 24, 1987

[87] PCT Pub. No.: WO87/03586
PCT Pub. Date: Jun. 18, 1987

[30] Foreign Application Priority Data
Dec. 9, 1985 [HU] Hungary .................. 4691/85

[51] Int. Cl.$^4$ .......................... C07D 403/04
[52] U.S. Cl. .................. 544/229; 544/363; 546/156
[58] Field of Search .............. 544/363, 229

[56] References Cited

U.S. PATENT DOCUMENTS 4,182,880  1/1980  Watanabe et al. ............ 546/13
4,528,287  7/1985  Itoh et al. ................... 544/363

FOREIGN PATENT DOCUMENTS 0090424 10/1983  European Pat. Off. ......... 544/363
59-80683  5/1984  Japan ....................... 544/229

OTHER PUBLICATIONS

Chem. Abstracts 103:123491p (1985) p. 730.
Chem. Abstracts 105:153293j (1986) p. 715.

Primary Examiner—Richard L. Raymond
Assistant Examiner—James H. Turnipseed
Attorney, Agent, or Firm—Herbert Dubno; Jonathan Myers

[57] ABSTRACT

The present invention relates to a process for the preparation of compounds of the general Formula I

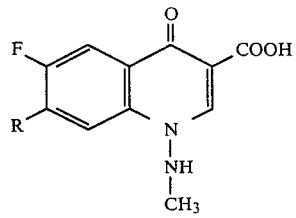

and pharmaceutically acceptable salts thereof (wherein R stands for piperazinyl or 4-methyl-piperazinyl) which comprises reacting a compound of the general Formula II

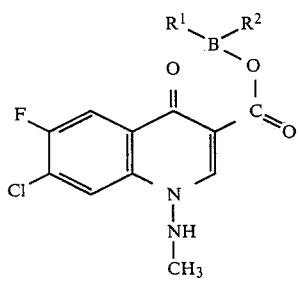

(wherein $R^1$ and $R^2$ stand for halogen; an aliphatic acyloxy group comprising 2–6 carbon atoms and optionally substituted by halogen; or an aromatic acyloxy group comprising 7–11 carbon atoms) with a piperazine of the general Formula III

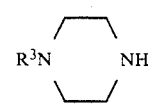

(wherein $R^3$ represent hydrogen or methyl) or a salt thereof, hydrolysing the compound of the general Formula IV

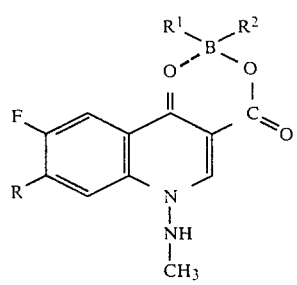

thus obtained (wherein R, $R^1$ and $R^2$ are as stated above) without or after hydrolysis and if desired converting the compound of the general Formula I thus obtained into a salt thereof or setting free the same from its salt.

The compounds of the general Formula I are known antibacterial agents.

The advantage of the process of the present invention is that it enables the preparation of the compounds of the general Formula I in a simple manner, with high yields and in a short reaction time.

5 Claims, No Drawings

1-METHYLAMINO-QUINOLINE-CARBOXYLIC ACID DERIVATIVES

FIELD OF THE INVENTION

This invention relates to a new process for the preparation of 7-substituted-6-fluoro-1-methylamino-4-oxo-1,4-dihydro-quinoline-3-carboxylic acid derivatives and pharmaceutically acceptable salts thereof.

BACKGROUND OF THE INVENTION

It is known that 6-fluoro-1-methylamino-4-oxo-1,4-dihydro-quinoline-3-carboxylic acid derivatives of the Formula I

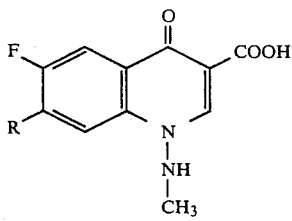

(wherein R stands for piperazinyl or 4-methyl-piperazinyl) have outstanding antibacterial effects (Journal of Medicinal Chemistry 1984, 27, 1103; Antimicrobal Agents and Chemotherapy 1984, 25, 377; 1984, 26, 104; 275; 421; 781; 933; 1985, 27, 4 and 499; European Journal of Clinical Microbiology 1984, 3, 344; Clin. Therapy 1984, 7, 73).

The said compounds can be prepared by reacting 6-fluoro-7-chloro-1-methylamino-4-oxo-1,4-dihydro-quinoline-3-carboxylic acid with a cyclic amine in pyridine or methoxyethanol, at the boiling point, under a protecting nitrogen atmosphere for 15–22 hours (European patent specification No. 90, 424; Japanese patent specification No. 84 01,468; Journal of Medicianl Chemistry 25, 377, 1984).

DESCRIPTION OF THE INVENTION

According to the present invention there is provided a process for the preparation of compounds of the Formula I and pharmaceutically acceptable salts thereof (wherein R stands for piperazinyl or 4-methyl-piperazinyl) which comprises reacting a compound of the Formula II

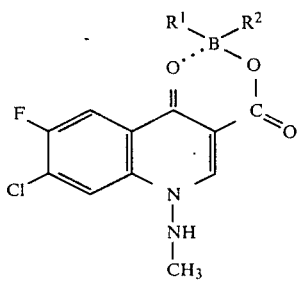

(wherein $R^1$ and $R^2$ stand for halogen; an aliphatic acyloxy group comprising 2–6 carbon atoms and optionally substituted by halogen; or an aromatic acyloxy group comprising 7–11 carbon atoms) with a piperazine of the Formula III

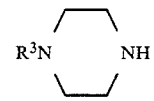

(wherein $R^3$ represents hydrogen or methyl) or a salt thereof, hydrolyzing the compound of the Formula IV

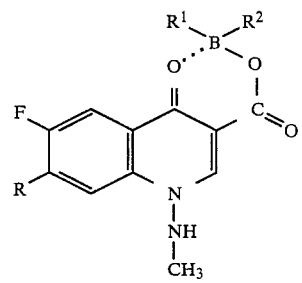

thus obtained (wherein R, $R^1$ and $R^2$ are as stated above) without or after hydrolysis and if desired converting the compound of the Formula I thus obtained into a salt thereof or liberating the compound from its salt.

The process of the present invention enables the preparation of the compounds of the general Formula I in a simple manner, with very high yields and in a short reaction time.

According to a preferred form of realization of the process of the present invention the borate derivatives of the Formula IV are converted into the desired quinoline-3-carboxylic acids of the Formula I without isolation.

The borate derivatives of the Formulae II and IV are new compounds.

The reaction of the borate derivative of the Formula II and the cyclic amine of the general Formula III may be carried out optionally in the presence of an inert organic solvent and an acid binding agent.

The inert organic solvent can be an acid amide (e.g. dimethyl formamide, dimethyl acetamide), a ketone (e.g. acetone, methyl ethyl ketone), an ether (e.g. dioxane, tetrahydrofuran, diethyl ether), an ester (e.g. ethyl acetate, methyl acetate, ethyl propionate), a sulfoxide (e.g. dimethyl sulfoxide), or an alcohol (e.g. methanol, ethanol, 1-decanol, butanol, etc.).

As acid binding agent e.g. organic or inorganic bases can be used. From the group of organic bases preferably trialkyl amines (e.g. triethyl amine, tributyl amine), cyclic amines (e.g. pyridine, 1,5-diazabicyclo(5.4.0)undec-5-ene, 1,5-diazabicyclo(4.3.0)non-5-ene, 1,4-diazabicyclo(2.2.2)octane) may be mentioned, while as inorganic base e.g. hydroxides or carbonates of alkali or alkaline earth metals may be applied. Thus it is preferred to use potassium carbonate, potassium hydrogen carbonate, sodium hydroxide, calcium hydroxide or an excess of the amine of the Formula III as acid binding agent.

The reaction of the borone derivative of the Formula II and the amine of the Formula III may be carried out at a temperature of 0°–200° C. during 0.5–10 hours, depending on the solvent used. The reaction time depends on the reaction temperature too. If the reaction temperature is raised, the reaction time can be shortened. The above reaction conditions are but preferable intervals, while other reaction conditions can be applied as well.

The borate of the Formula IV thus obtained is subjected to acidic or basic hydrolysis—after or without isolation—to yield the desired quinoline-3-carboxylic acid derivative of the Formula I. The reaction product of the Formula IV may be isolated e.g. by cooling the reaction mixture and separating the precipitated product e.g. by filtration or centrifuging.

Alkaline hydrolysis can preferably be carried out with the aid of a hydroxide or carbonate of an alkali metal or an alkaline earth metal hydroxide, preferably in the form of an aqueous solution. One may particularly preferably proceed by hydrolyzing the compound of the Formula IV by means of heating with an aqueous solution of sodium hydroxide, potassium hydroxide, sodium carbonate, potassium hydrogen carbonate, potassium carbonate or calcium hydroxide. Hydrolysis may also be accomplished with the aid of an organic base (e.g. triethyl amine).

Acidic hydrolysis may preferably be carried out by using an aqueous mineral acid solution. One may particularly advantageously proceed by heating with an aqueous hydrochloric acid, hydrogen bromide, sulfuric acid or phosphoric acid solution. Hydrolysis may also be accomplished with the aid of an organic acid (e.g. acetic acid, propionic acid, etc.).

The hydrolysis of the compounds of the Formula IV may also be carried out in the presence of a water-miscible organic solvent. For this purpose e.g. alcohols (e.g. methanol, ethanol), ketones (e.g. acetone), ethers (e.g. dioxane), acid amides (e.g. formamide, dimethyl formamide), sulfoxides (e.g. dimethyl sulfoxides) and pyridine may be used.

The quinoline-3-carboxylic acid derivatives of the Formula I thus obtained may be isolated, e.g. by adjusting the pH value to a suitable value and separating the precipitated crystals, for example, by centrifuging, filtration, or by lyophilization of the aqueous solution.

The quinoline-3-carboxylic acids of the Formula I can be converted into the pharmaceutically acceptable salts thereof. One may preferably form acid addition salts, e.g. salts formed with hydrogen halides, sulfonic acids, sulfuric acid or organic acids. Thus e.g. the chlorides, bromides, 4-methyl-phenyl-sulfonates, methanesulfonates, maleates, fumarates, benzonates, etc. can be formed. The compounds of the Formula I form salts with alkali or alkaline earth metals or other metal ions too; thus e.g. the sodium, potassium, magnesium, silver, copper salts, etc. can be prepared.

The hydrates (e.g. hemihydrates, trihydrates) of the compounds of the Formula I or pharmaceutically acceptable acid addition salts thereof may also prepared, if desired, by methods known per se.

The starting materials of the Formula II can be prepared e.g. by reacting 6-fluoro-7-chloro-1-methylamino-4-oxo-1,4-dihydro-quinoline-3-carboxylic acid (European patent specification No. 90,424) with various borone derivatives, e.g. with a borone derivative of the general Formula V

(wherein $R^1$, $R_2$ are as stated above and $R^4$ has the same meaning as $R^1$ or $R^2$) or fluoro boric acid in an aqueous or organic medium.

SPECIFIC EXAMPLES

Further details of the present invention are to be found in the following Examples without limiting the scope of protection to the said Examples.

EXAMPLE 1

A mixture of 6.87 g of 4-methyl-piperazine and 7.26 g of an anhydride of 6-fluoro-7-chloro-1-methylamino-4-oxo-1,4-dihydro-quinoline-3-carboxylic acid and difluoroboric acid formed with 36 ml of dimethyl sulfoxide is stirred at 110° C. for 3 hours. As the reaction proceeds yellow crystals precipitate gradually from the reaction mixture. The anhydride of 6-fluoro-1-methylamino-7-(4-methyl-piperazino)-4-oxo-1,4-dihydro-quinoline-3-carboxylic acid and difluoroboric acid thus formed is hydrolyzed without isolation from the reaction mixture as follows:

The reaction mixture is cooled to 80° C., whereupon 58 ml of a 6 weight/vol % aqueous sodium hydroxide solution are added within 5 minutes. The reaction mixture is heated to boiling and stirred for 2 hours under slight boiling. The solution is cooled to room temperature and the pH is adjusted to 7.2 by adding acetic acid. The crystalline mixture thus obtained is allowed to crystallize in a refrigerator overnight. Next morning the precipitated crystals are filtered, washed twice with 10 ml of water each and with 5 ml of methanol. Thus 5.8 g of 6-fluoro-1-methylamino-7-(4-methyl-piperazino)-4-oxo-1,4-dihydro-quinoline-3-carboxylic acid are obtained, yield 76.1%. Mp.: 300°–301° C. (decomposition; from dimethyl formamide).

| Analysis for the Formula $C_{16}H_{19}FN_4O_3$ | | |
| --- | --- | --- |
| calculated  C = 57.47%, | H = 5.72%, | N = 16.75%; |
| found  C = 57.71%, | H = 5.70%, | N = 16.68%. |

EXAMPLE 2

A mixture of 5.18 g of piperazine and 6.37 g of an anhydride of 6-fluoro-7-chloro-1-methylamino-4-oxo-1,4-dihydro-quinoline-3-carboxylic acid and difluoroboric acid formed with 32 ml of dimethyl sulfoxide is stirred at 110° C. for 3 hours. To the reaction mixture 51 ml of a 6 weight/vol % aqueous sodium hydroxide solution are added and the aqueous reaction mixture is stirred under slight boiling for 2 hours. The reaction mixture is filtered, the filtrate is evaporated in vacuo to two-thirds of its volume and the pH of the solution is adjusted to 6.5–7 by adding acetic acid. The reaction mixture is allowed to crystallize in a refrigerator overnight. Next morning the precipitated crystals are filtered, washed twice with 10 ml of water each and with 5 ml of methanol. Thus 5.3 g of 6-fluoro-1-ethylamino-7-piperazino-4-oxo-1,4-dihydro-quinoline-3-carboxylic acid are obtained. Yield: 82%. Mp.: 289°–291° C. (decomposition; from dimethyl formamide).

| Analysis for the Formula $C_{15}H_{17}FN_4O_3$ | | |
| --- | --- | --- |
| calculated  C = 56.24%, | H = 5.34%, | N = 12.49%; |
| found  C = 56.15%, | H = 5.37%, | N = 12.61%. |

A mixture of 1 g of 6-fluoro-1-methylamino-7-piperazino-4-oxo-1,4-dihydro-quinoline-3-carboxylic acid and 1.5 ml of water is treated with 0.6 g of p-toluene-sulfonic acid and the mixture is poured into 10 ml of methyl ethyl ketone. The reaction mixture is allowed to crystallize in a refrigerator overnight. Next morning the precipitated crystals are filtered and washed with methyl ethyl ketone. Thus 1.3 of the p-toluene-sulfonate salt of 6-fluoro-1-methylamino-7-piperazine-4-oxo-1,4-dihydro-quinoline-3-carboxylic acid are obtained, yield: 84.5%.

| Analysis for the Formula $C_{15}H_{17}FN_4O_3 \cdot C_7H_8O_3S$ | | | |
|---|---|---|---|
| calculated | C = 53.65%, | H = 5.11%, | N = 11.37%; |
| found | C = 53.89%, | H = 4.96%, | N = 11.25%. |

EXAMPLE 3

5 g of ethyl-6-fluoro-1-N-formyl-N-methylamino-7-chloro-4-oxo-1,4-dihydro-quinoline-3-carboxylate are stirred in 25 ml of a 50 weight/vol % aqueous solution of hydrogen fluoro borate at 90°–95° C. for 4 hours. After one hour and a half the precipitation of crystals gradually begins. The reaction mixture is cooled to room temperature and allowed to crystallize in a refrigerator overnight. Next morning the precipitated crystals are filtered and washed with some water. Thus 4.55 g of an anhydride of 6-fluoro-7-chloro-1-methylamino-4-oxo-1,4-dihydro-quinoline-3-carboxylic acid and difluoro boric acid are obtained. Yield: 93.4%. Mp.: 277° C. (decomposition).

| Analysis for the Formula $C_{11}H_7BF_3ClN_2O_3$ | | | |
|---|---|---|---|
| calculated | C = 41.48%, | H = 2.21%, | N = 8.79%; |
| found | C = 41.59%, | H = 2.34%, | N = 8.58%. |

EXAMPLE 4

0.797 g. of [6-fluoro-7-chloro-1,4-dihydro-1-(methylamino)-4-oxo-3-quinoline-carboxylate-$O^3,O^4$]bis(acetate-O)-boron and 0.6 g. of 1-methyl-piperazine are reacted in the presence of 5 ml. of dimethylsulfoxide at 110° C. for 2 hours. Then an aqueous solution of 6% by W/V sodium hydroxide (5.1 ml.) is added and stirred for another 1 hour at 110° C. The mixture is then cooled to 40° C. and the pH value is adjusted to 6.5 with 96% by W/V acetic acid. The mixture is then cooled to room temperature whereupon crystals are precipitated. The mixture is allowed to stand in a refrigerator overnight, then diluted with 15 ml. of water and the precipitated crystals are filtered, and washed with water and cold methanol. 0.56 g. (84%) of 6-fluoro-1,4-dihydro-1-(methylamino)-7-(4-methyl-piperazino)-4-oxo-3-quinoline-carboxylic acid is obtained. Decomposition after recrystallization from dimethylformamide at 293° C.

| Analysis for the formula $C_{16}H_{19}FN_4O_3$ | | | |
|---|---|---|---|
| calculated: | C = 57.48% | H = 5.73% | N = 16.76% |
| found: | C = 58.0% | H = 5.9% | N = 16.9% |

Preparation of the starting material 0.568 g. of boric acid and 3.28 g. of acetic acid anhydride are reacted in the presence of 1 mg. of zinc chloride while the temperature of the reaction mixture raises to 46° C. The white suspension is slowly heated at 100° C. and 2.0 g. of ethyl[7-chloro-6-fluoro-1,4-dihydro-1-(formylmethyl-amino)-4-oxo-3-quinoline-carboxylate] are added which had been previously dissolved in 10 ml. of 96% by W/V acetic acid. The reaction mixture is further heated for 2 hours at 110° C. The solution is cooled to room temperature and diluted with 40 ml of cold water. The precipitated crystals are filtered, washed with water and cold abs. ethanol, dried. 1.75 g. off-white, crystalline [6-fluoro-7-chloro-1,4-dihydro-1-(methyl-amino)-4-oxo-3-quinolinecarboxylate-$O^3,O^4$]-bis(acetate-O)-boron are obtained. Decomposition: 272° C.

Upon standing further 0.45 g. product crystallizes from the mother liquor.

| Analysis for the formula $C_{15}H_{13}BClFN_2O_7$ | | | |
|---|---|---|---|
| calculated: | C = 45.55% | H = 3.31% | N = 3.54% |
| found: | C = 45.2% | H = 3.2% | N = 3.6%. |

EXAMPLE 5

0.797 g. of [6-fluoro-7-chloro-1,4-dihydro-1-(methylamino)-4-oxo-3-quinolinecarboxylate-$O^3,O^4$]-bis-(acetate-O)-boron and 0.52 g. of piperazine are reacted in the presence of 5 ml. of dimethylsulfoxide at 110° C. for 2 hours. An aqueous solution of 6% by W/V sodium hydroxide (5 ml.) is then added to the reaction mixture which is then mildly boiled for 1 hour. The first crystals precipitate after 10 minutes. The reaction mixture is cooled to 40° C. and the pH is adjusted to 6.5 by adding 96% by W/V acetic acid whereafter the suspension is diluted. The precipitated crystals are filtered and washed with water and abs. ethanol. Yellowish-beige 6-fluoro-1,4-dihdyro-1-(methylamino)-7-piperazino-4-oxo-3-quinoline-carboxylic acid (0.42 g. 65%) is obtained.

| Analysis for the formula $C_{15}H_{17}FN_4O_3$ | | | |
|---|---|---|---|
| calculated: | C = 56.24% | H = 5.35% | N = 17.49% |
| found: | C = 55.9% | H = 5.5% | N = 17.8%. |

EXAMPLE 6

0.426 g. [6-fluoro-7-chloro-1,4-dihydro-1-(methylamino)-4-oxo-3-quinoline-carboxylate-$O^3,O^4$]-bis(propanoate-O)-boron and 0.3 g. of 1-methyl-piperazine are reacted in the presence of 2.5 ml. of dimethylsulfoxide for 2 hours at 110° C. Then an aqueous solution of 6% by W/V of sodium hydroxide (2.5 ml.) is added and the mixture is further heated for 1 hour at the above temperature. The reaction mixture is then cooled to 40° C. and the pH is adjusted to 6.5 by adding 96% by W/V acetic acid. Crystals immediately precipitate. The reaction mixture is allowed to stand overnight in the refrigerator and the precipitated crystals are filtered, washed with some water and methanol. Thus 0.22 g. (66%) of 6-fluoro-1,4-dihydro-1-(methylamino)-7-(4-methyl-piperazine)-4-oxo-3-quinoline-carboxylic acid is obtained, decomposing at 294° C. after recrystallization from dimethylformamide. No depression of the melting point is observed upon admixing the product at any ratio with the product of the previous Example.

Preparation of the starting material

1.

5 g. of ethyl-6-fluoro-1-(N-formyl-N-methyl-amino)-7-chloro-4-oxo-1,4-dihydro-quinoline-3-carboxylate are stirred in 25 ml of an 50 weight/vol % aqueous colution of hydrogen fluoroboric acid at 90°-95° C. for 4 hours. After one hour and a half the precipitation of crystals begins. The reaction mixture is cooled to room temperature, then placed into a refrigerator and allowed to crystallize overnight. The precipitated crystals are filtered next morning and washed with some water. Thus 4.55 g of an anhydride of 6-fluoro-7-chloro-1-(methylamino)-4-oxo-1,4-dihydro-quinoline-3-carboxylic acid and difluoro boric acid are obtained, yield: 93.4%. Mp.: 277° C. (decomposition).

| Analysis for the formula $C_{11}H_7BF_3ClN_2O_3$ | | | |
|---|---|---|---|
| calculated: | C = 41.48%, | H = 2.21%, | N = 8.79% |
| found: | C = 41.59%, | H = 2.34% | N = 8.58%. |

2.

5 g. of 6-fluoro-7-chloro-1-methylamino-4-oxo-1,4-dihydro-quinoline-3-carboxylic acid are stirred in 25 ml of a 50 weight/vol % aqueous solution of hydrogen fluoro boric acid at 80°-90° C. for 2 hours. After 45 minutes the precipitation of crystals begins. The reaction mixture is first cooled to room temperature and then allowed to crystallize for 2 hours at 0° C. The precipitated crystals are filtered, and washed with some water. Thus 4.95 g of an anhydride of 6-fluoro-7-chloro-1-methylamino-4-oxo-1,4-dihydro-quinoline-3-carboxylic acid and difluoro boric acid are obtained, yield 84.5%. Mp.: 277° C. (decomposition). A mixture of the product thus obtained with any amount of the compound prepared according to Example 1 shows no melting point depression.

3.

A mixture of 1.42 g of boric acid and 10.7 g of propionic anhydride is stirred at 100° C. for 15 minutes whereupon the reaction mixture is heated to boiling point. After 30 minutes the temperature of the reaction mixture is lowered to 110° C. and 4.2 g of 6-fluoro-7-chloro-1-methylamino-4-oxo-1,4-dihydro-quinoline-3-carboxylic acid are added. After some minutes the precipitation of crystals begins. The reactin mixture is stirred at 110° C. for 2 hours, cooled to 10° C., whereupon 20 ml of water and 20 ml of ethanol are added to the crystalline suspension. The reaction mixture is allowed to crystallize in a refrigerator overnight. The precipitated crystals are filtered, washed with water and dried. Thus 6.12 g of (6-fluoro-7-chloro-1-methylamino-4-oxo-1,4-dihydro-quinoline-3-carboxylic-acid-borone-dipropionyloxy)-anhydride are obtained.

Yield: 93.5%, mp.: 215° C. (decomposition).

| Analysis for the formula $C_{17}H_{17}BFClN_2O_7$ | | | |
|---|---|---|---|
| calculated: | C = 47.86%, | H = 4.01%, | N = 6.56%, |
| found: | C = 48.07%, | H = 3.87%, | N = 6.48%. |

What we claim is:
1. A compound of the Formula (IV)

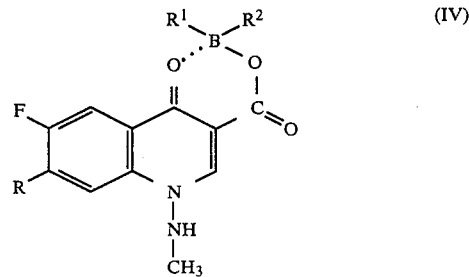

wherein
R is piperazinyl or 4-methyl-piperazinyl;
$R^1$ and $R^2$ are each halogen, $C_2$ to $C_6$ aliphatic acyloxy optionally substituted by halogen, or $C_7$ to $C_{11}$ aromatic acyloxy.

2. The compound of the Formula (IV) defined in claim 1 wherein $R^1$ and $R^2$ are each halogen.

3. The compound of the Formula (IV) defined in claim 1 wherein $R^1$ and $R^2$ are each $C_2$ to $C_6$ aliphatic acyloxy.

4. The compound of the Formula (IV) defined in claim 1 wherein $R^1$ and $R^2$ are each fluoro.

5. The compound of the Formula (IV) defined in claim 1 wherein $R^1$ and $R^2$ are each acetoxy or propionyloxy.

* * * * *

UNITED STATES PATENT AND TRADEMARK OFFICE
CERTIFICATE OF CORRECTION

PATENT NO. : 4,871,849
DATED : 3 October 1989
INVENTOR(S) : Istvan HERMECZ et al It is certified that error appears in the above-identified patent and that said Letters Patent is hereby corrected as shown below:

On the title page:

Item [75] The third inventor's name to read:
-- Lelle VASVÁRI --;

The tenth inventor's name to read:
-- Anikó Pajor --.

Signed and Sealed this

Twentieth Day of November, 1990

Attest:

HARRY F. MANBECK, JR.

*Attesting Officer*  *Commissioner of Patents and Trademarks*